United States Patent [19]

Fäh et al.

[11] 4,404,388

[45] * Sep. 13, 1983

[54] PROCESS FOR PRODUCING 2-CHLOROPYRIDINES

[75] Inventors: Hansjakob Fäh, Ormalingen; Alfred Grieder, Böckten, both of Switzerland

[73] Assignee: Ciba-Geigy Corporation, Ardsley, N.Y.

[ * ] Notice: The portion of the term of this patent subsequent to Sep. 1, 1998, has been disclaimed.

[21] Appl. No.: 292,847

[22] Filed: Aug. 14, 1981

[51] Int. Cl.³ .............. C07D 213/02; C07D 213/26; C07D 213/55
[52] U.S. Cl. .................. 546/345; 546/318; 203/58
[58] Field of Search ............... 546/345, 318

[56] References Cited

U.S. PATENT DOCUMENTS

4,287,347 9/1981 Fah et al. .................. 546/345

FOREIGN PATENT DOCUMENTS

622170 3/1981 Switzerland ............ 71/94

OTHER PUBLICATIONS

Annlen der Chemie, 486, 71–80, 1931.

*Primary Examiner*—Alan L. Rotman
*Attorney, Agent, or Firm*—Karl F. Jorda

[57] ABSTRACT

Production of 2-chloropyridines of the formula I

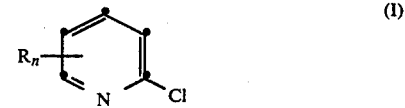

wherein
R independently of one another is $C_1$–$C_4$-alkyl, $C_1$–$C_4$-halogenalkyl, halogen or carboxyl and
n is zero or a number from one to four, with the proviso that at most two substituents R can be alkyl, halogenoalkyl or carboxyl at the same time, and that if R is chlorine and n is two, one of them must not occupy the 3- or 5-position of the pyridine ring, by reacting a 2-pyridone of the formula (II)

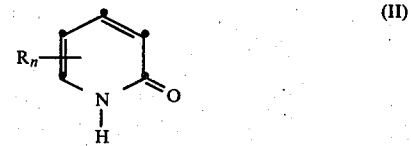

wherein R and n have the meanings given above at 30°–150° C. with phosgene in the presence of an N,N-disubstituted formamide of the formula III

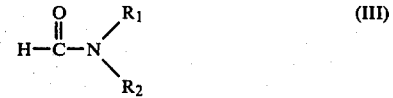

in which $R_1$ and $R_2$ can be identical or different and are each an alkyl group having 1 to 4 carbon atoms, or $R_1$ and $R_2$ together with the nitrogen atom form the pyrrolidino, piperidino or morpholino ring, and in the presence of an inert solvent.

2-chloropyridines are valuable intermediates for producing herbicidally active α-[4-pyrid-2-yloxy)-phenoxy]-alkanecarboxylic acids and derivatives thereof.

16 Claims, No Drawings

PROCESS FOR PRODUCING 2-CHLOROPYRIDINES

The present invention relates to a process for producing 2-chloropyridines.

2-Chloropyridines are valuable intermediates for producing herbicidally active α-[4-(pyrid-2-yloxy)-phenoxy]-alkanecarboxylic acids and derivatives thereof. The production and use of such α-[4-pyrid-2-yloxy)-phenoxy]-alkanecarboxylic acids and derivatives thereof are described for example in the Swiss Pat. Specif. No. 622 170.

The production of 2-chloropyridines from N-alkyl-2-pyridones with phosgene in toluene as solvent or without a solvent is known. The process comprises introducing a N-alkyl-2-pyridone into a toluene solution of phosgene, and heating the mixture in a closed system to 150°–180° C., or bubling phosgene through the melt of such a N-alkylpyridone at 200° C. The pyridines are obtained in this manner in a yield of 50 to 90% of theory (Ann. Chem. 486, 71–80, 1931). The N-alkyl-2-pyridones required as starting materials for carrying out this process are obtained by alkylation of the corresponding 2-pyridones.

The known process is disadvantageous in so far as the 2-pyridones firstly have to be converted into N-alkyl-2-pyridones, and the N-alkyl group of this is removed again in the subsequent reaction with phosgene to give corresponding pyridines. In this process, there is thus intermediately introduced a group which is not present at all in the final product. This is uneconomical with respect to the necessity of having to carry out an additional process step, with respect to the costs associated with that, with respect to the losses in yield resulting from this additional step, and finally with respect to the consumption of chemicals which do not contribute towards the structural synthesis of the end products. Furthermore, the high reaction temperature at which the process is performed necessitates carrying out the reaction in a closed system under pressure or at even higher temperatures when the process is carried out in the melt, and as a result of this there is a considerable increase in the expenditure on equipment required to carry out the process on a large commercial scale.

The aim of the present invention therefore is to avoid the disadvantages of the known procedure, and to provide a process by which 2-chloropyridines can be produced on a commercial scale in a simple and economic manner.

The proposal according to the present invention is to produce a 2-chloropyridine of the formula I

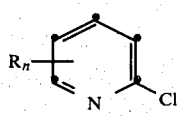
(I)

wherein
R independently of one another is $C_1$–$C_4$-alkyl, $C_1$–$C_4$-halogenalkyl, halogen or carboxyl and
n is zero or a number from one to four, with the proviso that at most two substituents R can be alkyl, halogenoalkyl or carboxyl at the same time, and that if R is chlorine and n is two, one of them must not occupy the 3- or 5-position of the pyridine ring, by reacting a 2-pyridone of the formula (II)

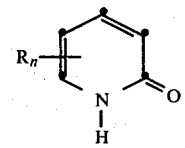
(II)

wherein R and n have the meanings given above at 30°–150° C. with phosgene in the presence of an N,N-disubstituted formamide of the formula III

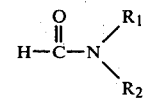
(III)

in which $R_1$ and $R_2$ can be identical or different and are each an alkyl group having 1 to 4 carbon atoms, or $R_1$ and $R_2$ together with the nitrogen atom form the pyrrolidino, piperidino or morpholino group, and in the presence of an inert solvent.

Preferred compounds to be synthesized by the process of the invention are those of the narrower formula IV

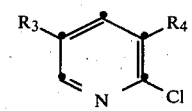
(IV)

wherein
$R_3$ and $R_4$ independently of one another represent chlorine, bromine, $C_1$–$C_4$-alkyl or $C_1$–$C_4$-halogenalkyl, with the proviso that $R_3$ and $R_4$ are not chlorine at the same time.

Even more preferred are those compounds of formula IV wherein $R_3$ is bromine, methyl, ethyl or $C_1$–$C_2$-halogenoalkyl and $R_4$ is chlorine or bromine.

Especially preferred compounds are those wherein $R_3$ is methyl or trifluoromethyl and $R_4$ is chlorine or bromine.

Preferred individual compounds prepared by the process of the invention are 3-bromo-2-chloro-5-methyl-pyridine and 2,3-dichloro-5-trifluoromethyl-pyridine.

The reaction of the 2-pyridones is performed within the above-given temperature range of 30°–150° C., preferably at 50°–90° C. The reaction is performed as a rule under normal pressure. It may be necessary to carry out the reaction in a closed system under pressure only when a relatively low-boiling solvent is used and a high reaction temperature applied, for example a temperature in the range of 100°–150° C. Suitable solvents in which the process according to the invention can be performed are in general those solvents which under the reaction conditions are inert to the reactants. Suitable solvents are in particular: aromatic hydrocarbons, such as benzene, toluene or xylene; aliphatic hydrocarbons, such as hexane, heptane or petroleum ether; cycloaliphatic hydrocarbons, such as cyclopentane and cyclohexane; halogenated aromatic hydrocarbons, such as chlorobenzene or o-dichlorobenzene; halogenated aliphatic hydrocarbons, such as methylene chloride, chloroform, carbon tetrachloride, 1,2-dichloroethane and trichloroethylene, as well as aliphatic carboxylic acid esters, such as ethyl acetate and isopropyl acetate. A preferred solvent is toluene.

Suitable N,N-disubstituted formamides are N,N-dimethylformamide, N,N-diethylformamide, N,N-dipropylformamide, N,N-dibutylformamide, N-methyl-N-butylformamide, as well as N-formylpyrrolidine, N-formylpiperidine and N-formylmorpholine. A preferred N,N-disubstituted formamide is N,N-dimethylformamide. The N,N-disubstituted formamides are used in amounts of 0.01–1.0 mol per mol of 2-pyridone, preferably 0.05 to 0.15 mol per mol of 2-pyridone.

Phosgene is used according to the invention generally in at least an equimolar amount of in excess. The amount advantageously used is 1.0 to 1.5 mols of phosgene per mol of 2-pyridone. The amount preferably used is 1.0 to 1.3 mols of phosgene per mol of 2-pyridone. After completion of the reaction, the unreacted phosgene is reacted with an aqueous caustic solution, such as with an aqueous sodium hydroxide solution or with aqueous ammonia.

The reaction of the 2-pyridones with phosgene takes as a rule 1–5 hours, and in most cases it is completed in 2–4 hours.

According to a preferred embodiment of the process of the invention, the 2-pyridone is suspended in toluene, the water present is separated by azeotropic distillation, 0.05–0.15 mol of N,N-dimethylformamide per mol of 2-pyridone is added, and 1.0–1.3 mols of phosgene per mol of 2-pyridone are introduced at 75°–80° C. After the addition of phosgene has been completed, the reaction mixture is allowed to react for a further one hour at 75°–80° C., and the excess phosgene is subsequently reacted with water and aqueous ammonia. The phases are afterwards separated, the solvent is distilled off from the organic phase, and the 2-chloropyridine is obtained as a melt or a destillable liquid.

It becomes possible by the process according to the invention to produce 2-chloropyridines on a commercial scale in a simple and economic manner. The process avoids the N-methylation of the 2-pyridones which the known process necessitates, and can be performed under considerably milder conditions. The total yield is increased, and the necessary expenditure on equipment to carry out the process is reduced.

The process according to the invention is further illustrated by the following Examples.

EXAMPLE 1

131.3 g (0.7 mole) of 3-bromo-5-methyl-2-pyridone, 700 ml of toluene and 5.7 g (78 mmole) of N,N-dimethylformamide are placed into a 1.5 liter reactor. The mixture is then heated with stirring to 75°–80° C., and at this temperature 97.4 g (0.98 mole) of phosgene are introduced in the course of 2 hours. After completion of the addition of phosgene, stirring is continued for 1 hour. The reaction mixture is afterwards cooled to 15°–20° C., and is subsequently stirred up with 84.0 ml of water and 60.0 g of 30% aqueous ammonia. After separation of the aqueous phase, the toluene is destilled off at reduced pressure. The yield as residue is 128.4 g (88.8% of theory) of 3-bromo-2-chloro-5-methyl-pyridine in form of a melt, which solidifies on cooling, m.p. 63°–64° C.

EXAMPLE 2

296.3 g (1.5 mole) of 3-chloro-5-trifluoromethyl-2-pyridone, 1.5 liter of toluene and 12.2 g (0.167 mole) of N,N-dimethylformamide are placed into a 3 liter reactor. The mixture is then heated with stirring to 75°–80° C., and at this temperature 203 g (2.1 mole) of phosgene are introduced in the course of 2–3 hours. After completion of the addition of phosgene, stirring is continued for 1 hour. The reaction mixture is cooled afterwards to 20°–25° C., and is subsequently stirred up with 180 ml of water and 129 g of 30% aqueous ammonia. After separation of the aqueous phase, the toluene is destilled off at normal pressure. The yield as residue in 305 g (94% of theory) of 2,3-dichloro-5-trifluoromethyl-pyridine in form of an oil, b.p. 76°–79° C./55 mb.

The following compounds can be prepared analogously:

| Comp. No. | $R_n$ |
| --- | --- |
| 1 | 3-Br, 5-Ch$_3$ |
| 2 | 3-Cl, 5-CF$_3$ |
| 3 | 3-Cl, 5-CH$_3$ |
| 4 | 3-Br, 5-CF$_3$ |
| 5 | 2,3,6-Cl |
| 6 | 3-Br, 5-Cl |
| 7 | 3,5-Br |
| 8 | 3,4,5,6-Cl |
| 9 | 3-CH$_3$, 5-CF$_3$ |
| 10 | 3-CF$_3$, 5-CF$_3$ |
| 11 | 5-CF$_3$ |
| 12 | 5-CH$_3$ |
| 13 | 3-F, 5-Cl |
| 14 | 5-Cl, 3-F |
| 15 | 3-Cl, 5-COOH |

What is claimed is:

1. A process for producing a 2-chloropyridine of the formula I,

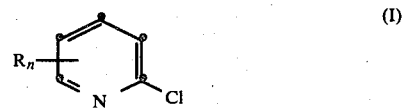

wherein
R independently of one another is $C_1$–$C_4$-alkyl, $C_1$–$C_4$-halogenalkyl, halogen or carboxyl and
n is zero or a number one to four, with the proviso that at most two substituents R can be alkyl, halogenalkyl or carboxyl at the same time, and that if R is chlorine and n is two one of them must not occupy the 3- or 5-position of the pyridine ring, by reacting a 2-pyridone of the formula (II)

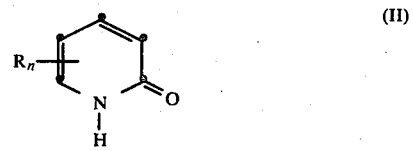

wherein R and n have the meanings given above at 30°–150° C. with phosgene in the presence of an N,N-disubstituted formamide of the formula III

in which $R_1$ and $R_2$ can be identical or different and are each an alkyl group having 1 to 4 carbon atoms, or $R_1$ and $R_2$ together with the nitrogen atom form the pyrrolidino, piperidino or morpholino ring, and in the presence of an inert solvent.

2. A process according to claim 1 for producing compounds of the narrower formula IV

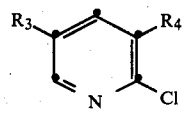

wherein $R_3$ and $R_4$ independently of one another represent chlorine, bromine, $C_1$–$C_4$-halogenoalkyl, with the proviso that $R_3$ and $R_4$ are not chlorine at the same time.

3. A process according to claim 2 wherein $R_3$ is bromine, methyl, ethyl or $C_1$–$C_2$-halogenoalkyl and $R_4$ is chlorine or bromine.

4. A process according to claim 2 wherein $R_3$ is methyl or trifluoromethyl and $R_4$ is chlorine or bromine.

5. A process according to claim 1 for producing 3-bromo-2-chloro-5-methyl-pyridine.

6. A process according to claim 1 for producing 2,3-dichloro-5-trifluoromethyl-pyridine.

7. A process according to claim 1, wherein the reaction of a 2-pyridone with phosgene is performed at a temperature of 50°–90° C.

8. A process according to claim 1, wherein the inert solvent used is an aromatic hydrocarbon, an aliphatic hydrocarbon, a cycloaliphatic hydrocarbon, a halogenated aromatic hydrocarbon, a halogenated aliphatic hydrocarbon or an aliphatic carboxylic acid ester.

9. A process according to claim 1, wherein the solvent used is toluene.

10. A process according to claim 1, wherein the N,N-disubstituted formamide used is N,N-dimethylformamide, N,N-diethylformamide, N,N-dipropylformamide, N,N-dibutylformamide, N-methyl-N-butylformamide, N-formylpyrrolidine, N-formylpiperidine or N-formylmorpholine.

11. A process according to claim 1, wherein the N,N-disubstituted formamide used is N,N-dimethylformamide.

12. A process according to claim 1, wherein the N,N-disubstituted formamide is used in an amount of 0.01–1.0 mol per mol of 2-pyridone.

13. A process according to claim 1, wherein the N,N-disubstituted formamide is used in an amount of 0.05–0.15 mol per mol of 2-pyridone.

14. A process according to claim 1, wherein 1.0–1.5 mols of phosgene are used per mol of 2-pyridone.

15. A process according to claim 1, wherein 1.0–1.3 mols of phosgene are used per mol of 2-pyridone.

16. A process according to claim 1, wherein 2-pyridone is suspended in toluene, the water present is separated by azeotropic distillation, 0.05–0.15 mol of N,N-dimethylformamide per mol of 2-pyridone is added, 1.0–1.3 mols of phosgene per mol of 2-pyridone are introduced at 75°–80° C., the reaction mixture is stirred for a further 1 hour, the excess phosgene is reacted with aqueous ammonia, the phases are separated, and from the organic phase is obtained, after removal of the solvent by distillation, the formed 2-chloropyridine in the form of a melt or a distillable liquid.

* * * * *